(12) United States Patent
Berg et al.

(10) Patent No.: US 7,894,663 B2
(45) Date of Patent: Feb. 22, 2011

(54) METHOD AND SYSTEM FOR MULTIPLE VIEW VOLUME RENDERING

(75) Inventors: Sevald Berg, Horten (NO); Stein Inge Rabben, Sofiemyr (NO); Sigmund Frigstad, Trondheim (NO)

(73) Assignee: General Electric Company, Schenectady, NY (US)

( * ) Notice: Subject to any disclaimer, the term of this patent is extended or adjusted under 35 U.S.C. 154(b) by 906 days.

(21) Appl. No.: 11/772,147

(22) Filed: Jun. 30, 2007

(65) Prior Publication Data
US 2009/0003665 A1 Jan. 1, 2009

(51) Int. Cl.
G06K 9/00 (2006.01)
G06T 15/00 (2011.01)
(52) U.S. Cl. ........................ 382/154; 382/128; 345/419
(58) Field of Classification Search ................. 382/131, 382/128, 154; 345/419–420
See application file for complete search history.

(56) References Cited

U.S. PATENT DOCUMENTS

| | | | | |
|---|---|---|---|---|
| 5,839,440 A | * | 11/1998 | Liou et al. | 600/431 |
| 6,159,150 A | * | 12/2000 | Yale et al. | 600/437 |
| 6,280,387 B1 | * | 8/2001 | Deforge et al. | 600/454 |
| 7,773,074 B2 | * | 8/2010 | Arenson et al. | 345/173 |
| 2006/0034513 A1 | * | 2/2006 | Cai et al. | 382/173 |
| 2006/0197780 A1 | | 9/2006 | Watkins et al. | |
| 2007/0008317 A1 | * | 1/2007 | Lundstrom | 345/424 |
| 2007/0046661 A1 | * | 3/2007 | Ma et al. | 345/419 |
| 2008/0123800 A1 | * | 5/2008 | Joshi et al. | 378/4 |

OTHER PUBLICATIONS

Deischinger et al., System and method for automatically obtaining ultrasound image planes based on patient specific information, U.S. Appl. No. 11/434,432, filed May 15, 2006.

* cited by examiner

*Primary Examiner*—Daniel G Mariam

(57) ABSTRACT

A method and system for multiple view volume rendering are provided. The method includes identifying a plurality of view directions relative to an image of an object and automatically volume rendering a volumetric data set based on the plurality of view directions. The method further includes generating an image for each view direction using the rendered data.

19 Claims, 7 Drawing Sheets

METHOD AND SYSTEM FOR MULTIPLE VIEW VOLUME RENDERING

BACKGROUND OF THE INVENTION

This invention relates generally to medical imaging systems, and more particularly, to providing multiple volume renderings from the same data set acquired by a medical imaging system.

Medical imaging systems are used in different applications to image different regions or areas (e.g., different organs) of patients. For example, ultrasound imaging may be used to generate images of a heart. These images are then displayed for review and analysis by a user. The images also may be modified or adjusted to better view or visualize different regions or objects of interest.

Visualization by volume rendering is a known technique to produce realistic images (e.g., three-dimensional images) based on a three-dimensional data set. For example, three-dimensional data may be projected onto a two-dimensional image in a given viewing direction. The projection can be performed using known algorithms, for example, using ray-tracing algorithms and advanced lighting models. A user is typically able to adjust the view direction for the image such that, for example, an imaged object may be viewed from different angles or perspectives. For example, a user can move an ultrasound probe in different directions and angles to acquire and view images of a heart at different locations around the heart. A user also may manipulate stored data to generate different views.

In volume imaging, another important functionality is the ability to crop parts of the imaged object in order to look inside the object. The crop function can be performed in different ways. Cropping is commonly performed by defining a plane that cuts into the imaged object and the part of the object on one side of that plane is removed from the rendering.

When visualizing objects using volume imaging challenges arise. For example, a challenge with visualization of the human heart using volume ultrasound is to navigate in the volumetric data and identify anatomical structures from different angles in order to produce clinically relevant views. Typically, an operator manually defines single rendering views by cutting the volume at random locations with no relation to other previously defined views. For example, an operator generates one view of a heart by cropping the image to generate a single view and then rotating and/or translating the image to another view and then cropping the image again at another location to generate another view. This process is repeated until multiple different images defining different views are generated.

Thus, the manual process to define and generate different views of an image is tedious and time consuming. Additionally, the views generated may not capture the entire region or regions of interest from different perspectives, thereby potentially resulting in excluding clinically relevant portions of the image and possible improper diagnosis.

BRIEF DESCRIPTION OF THE INVENTION

In accordance with an embodiment of the invention, a method for generating multiple image views of an object is provided. The method includes identifying a plurality of view directions relative to an image of an object and automatically volume rendering a volumetric data set based on the plurality of view directions. The method further includes generating an image for each view direction using the rendered data.

In accordance with another embodiment of the invention, a method for visualization of multiple volume renderings of volumetric data set is provided. The method includes identifying at least one crop plane on the volumetric data set and automatically generating a plurality of different views using the volumetric data set based on the at least one crop plane. The method further includes displaying on a single display images of the different views.

In yet another embodiment of the invention, an ultrasound imaging system is provided that includes a probe configured to acquire three-dimensional (3D) ultrasound image data defining a 3D ultrasound data set. The ultrasound imaging system further includes a multiple volume rendering module configured to volume render different image views of the 3D ultrasound data set based on at least one view direction and at least one crop plane.

DETAILED DESCRIPTION OF THE INVENTION

Figure 1:
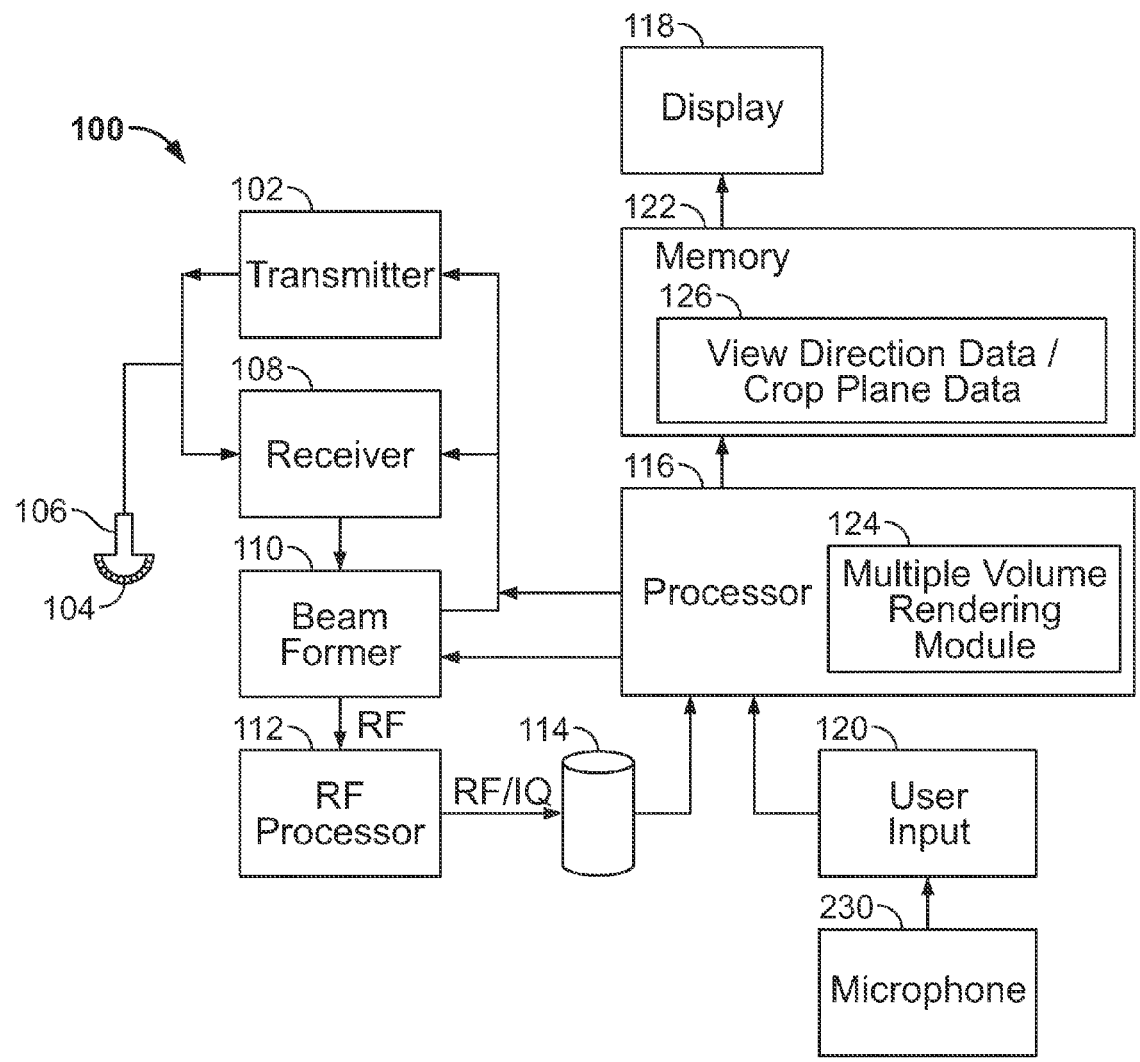
FIG. 1 is a block diagram of an ultrasound system formed in accordance with an embodiment of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates a block diagram of an ultrasound system 100. The ultrasound system 100 includes a transmitter 102 that drives transducer elements 104 within a probe 106 to emit pulsed ultrasonic signals into a body. The ultrasonic signals or transmit beams are back-scattered from structures in the body, like blood cells or muscular tissue, to produce echoes or return beams that return to the transducer elements 104. The returning echoes are converted by the transducer elements 104 back to electrical energy that is received by a receiver 108. The received signals are passed through a beamformer 110 that performs beamforming and outputs an RF signal. It should be noted that transmit beamforming also be provided by combining the transducer element signals to perform steering and focusing of the beam. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114, for example, an RF/IQ buffer for temporary storage.

A user input 120 (that may be configured as a user interface with a keyboard, trackball, control buttons, etc.) may be used to control operation of the ultrasound system 100, including, to control the input of patient data and scan parameters, to select or define different view directions or crop planes, and may also include using voice commands provided via a microphone 130. Other components may be provided, for example, a set of user controls may be configured for controlling the ultrasound system 100 and may be provided as part of a touch screen or panel, and as manual inputs, such as user operable switches, buttons, and the like. The set of user controls may be manually operable or voice operated.

The ultrasound system 100 also includes a processor 116 (e.g., a processor module) to process the acquired ultrasound information (i.e., RF signal data or IQ data pairs) and prepare frames of ultrasound information for display on a display 118. The processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 114 during a scanning session and processed in less than real-time in a live or off-line operation. An image memory 122 is included for storing processed frames of acquired ultrasound information that are not scheduled to be displayed immediately. The image memory 122 may comprise any known data storage medium.

A multiple volume rendering module 124 (hereafter referred to as a volume rendering module 124) may access view direction data/crop plane data 126 stored within the memory 122 to automatically visualize multiple volume renderings of an object (e.g., a heart) based on a three-dimensional (3D) ultrasound data set. The volume rendering module 124 may be implemented in hardware, software or a combination thereof. Volume rendering and calculations, as well as the display of crop planes and view planes can be implemented using a specialized graphics hardware and/or processor, in a graphics processor unit (GPU), or in software using any type of processor. The multiple renderings are generated from a single data set stored in memory (e.g., fixed memory or removable memory) that may be defined by one or more crop planes selected by a user and that also may be linked, associated or otherwise connected as described in more detail below.

The display 118 includes one or more monitors that present patient information, including diagnostic ultrasound images to the user for diagnosis and analysis. The display 118 automatically displays multiple views, for example, multiple rendering views of a heart, which may be in a quad format, from the 3D ultrasound data set stored in the memory 114 or 122 (or other memory device). Specialized 3D displays also can be used to display the volume rendered images. One or both of the memory 114 and memory 122 may store three-dimensional data sets of the ultrasound data, where such 3D data sets are accessed to present 2D and 3D images. A 3D ultrasound data set is mapped into the corresponding memory 114 or 122, as well as one or more image views. The position and orientation of the views may be controlled based on commands from the user input 120.

The system 100 obtains volumetric data sets by various techniques (e.g., 3D scanning, real-time 3D imaging, volume scanning, 2D scanning with transducers having positioning sensors, freehand scanning using a Voxel correlation technique, 2D or matrix array transducers and the like). For 2D scanning, the transducer 106 is moved, such as along a linear or arcuate path, while scanning a region of interest (ROI). At each linear or arcuate position, the transducer 106 obtains scan planes that are stored in the memory 114. For 3D scanning with a 2D array of transducers, a volume is scanned in real time covering portions of or the entire region of interest.

It should be understood that the functionality discussed with respect to the system 100 is not limited to any ultrasound system type. For example, the system 100 may be housed within a cart-based system or may be implemented in a smaller, portable system as discussed in FIG. 2.

Figure 2:
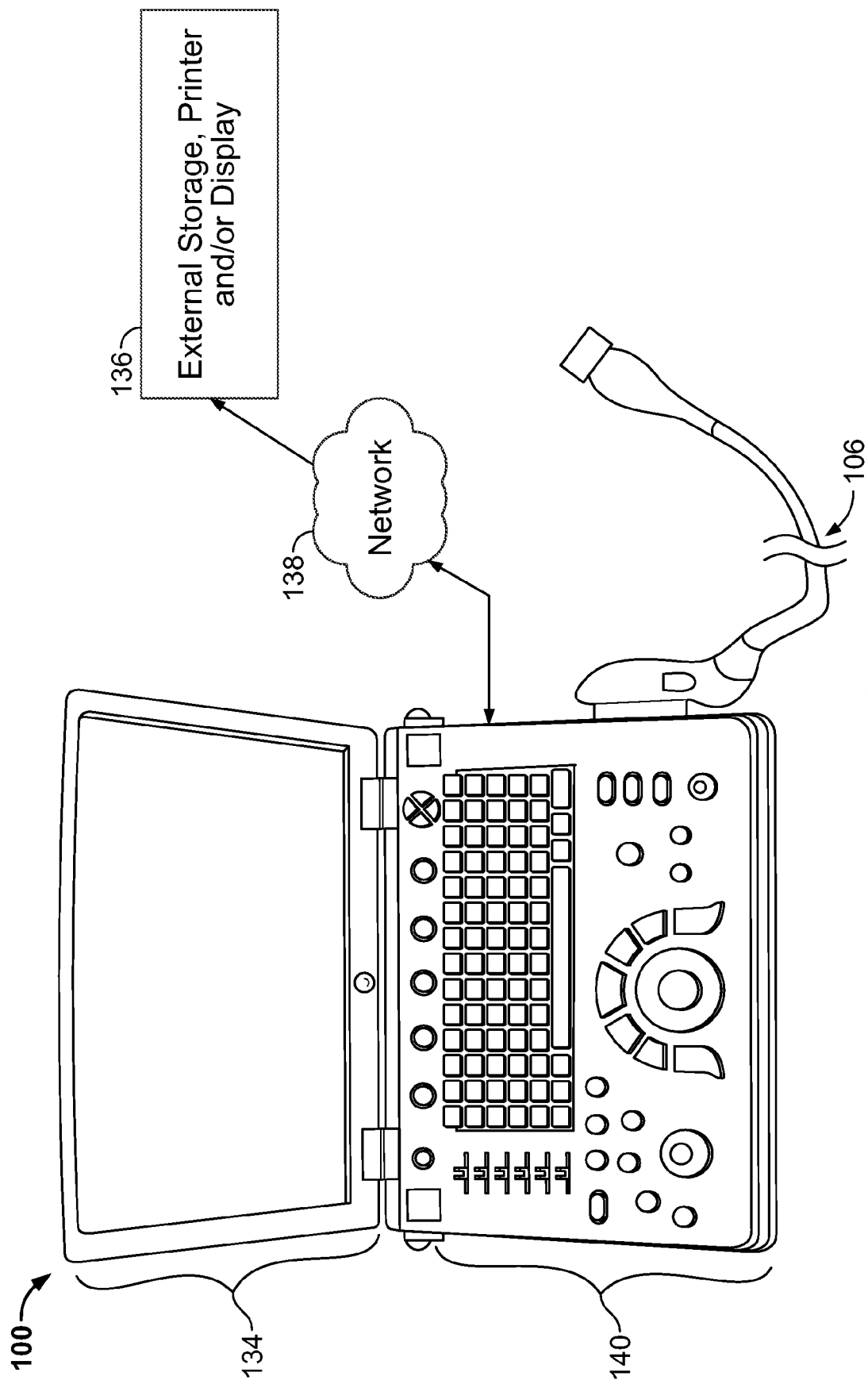
FIG. 2 illustrates a miniaturized ultrasound system formed in accordance with an embodiment of the invention.

FIG. 2 illustrates a miniaturized ultrasound system 100 having the probe 106 configured to acquire ultrasonic data. As used herein, "miniaturized" means that the ultrasound system is a handheld or hand-carried device or is configured to be carried in a person's hand, pocket, briefcase-sized case, backpack or the like. For example, the ultrasound system 100 may be a hand-carried device having a size of a typical laptop computer. An integrated display 134 (e.g., an internal display) is also provided and is configured to display one or more medical images.

The ultrasonic data may be sent to an external device 136 via a wired or wireless network 133 (or direct connection, for example, via a serial or parallel cable or USB port). In some embodiments, the external device 136 may be a computer or a workstation having a display. Alternatively, the external device 136 may be a separate external display or a printer capable of receiving image data from the hand-carried ultrasound imaging system 100 and of displaying or printing images that may have greater resolution than the integrated display 134.

A user interface 140 (that may also include the integrated display 134) is provided to receive commands from an operator. The acquired image data may be acquired in a higher resolution than that displayable on the integrated display 134.

As another example, the ultrasound system 100 may be a pocket-sized ultrasound system. The pocket-sized ultrasound system may include a display, a user interface (i.e., keyboard) and an input/output (I/O) port for connection to the probe (all not shown). It should be noted that the various embodiments may be implemented in connection with a miniaturized ultrasound system having different dimensions, weights, and power consumption.

The various embodiments may be implemented in connection with any diagnostic imaging system, for example, different types of medical imaging systems, such as an ultrasound imaging system, an x-ray imaging system, a computed-tomography (CT) imaging system, a single photon emission computed tomography (SPECT) system, a positron emission tomography (PET) imaging system, a nuclear medicine imaging system, a magnetic resonance imaging (MRI) system, and combinations thereof (e.g., a multi-modality imaging system), among others. Moreover, the various embodiment are not limited to medical imaging systems or imaging systems for imaging human subjects, but may include non-medical systems for imaging non-human objects and for performing non-destructive imaging or testing, security imaging (e.g., airport security screening), etc.

In various embodiments, the user input 120 may be used to select one or more rendering views by defining one or more view directions and/or crop planes (which also may be referred to as cut planes). For example, one or more planes may be designated and include the orientation and position of the plane. Additional parameters may be defined to, for example, adjust the size and shape of the planes, translate and rotate the position of the planes relative to a reference coordinate system and the like. One or more view directions are defined with volume rendering automatically performed from a single set of 3D ultrasound data stored in memory. For example, the data may be stored as the view direction data/crop plane data 126 (shown in FIG. 1). Thus, multiple views may be defined with the corresponding images automatically rendered and linked. For example, standard echocardiographic views of a heart may be simultaneously generated and then displayed with various embodiments of the invention.

The volume rendering module 124 maps the one or more view directions or crop plane into a 3D ultrasound data set and automatically renders the different views accordingly. The display 118 selectively displays the image views associated with the rendered image data. The memory 114 or 122 stores the view position data and/or crop plane data for one or more views (e.g., location coordinates). Optionally, the memory 114 or 122 may store, in connection with the position and crop plane data for the views, information other than coordinates of the view direction and planes that define the multiple views, for example, a selected point or region within the image.

Figure 3:
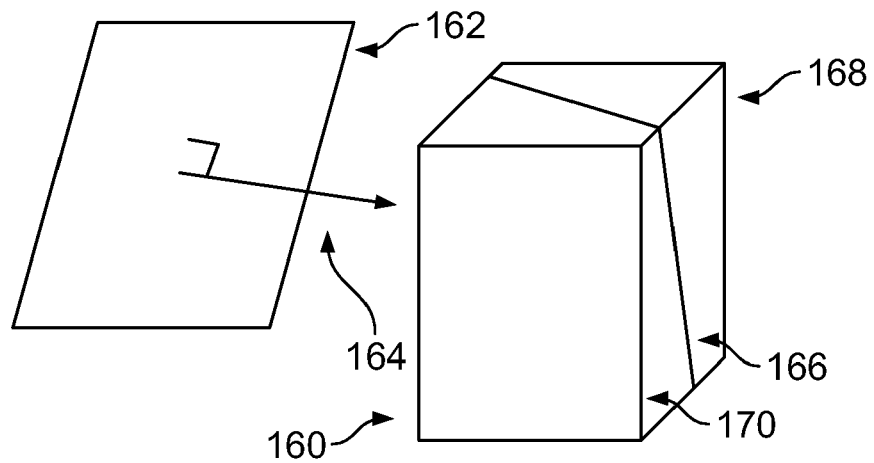
FIG. 3 is a diagram illustrating a view plane and a crop plane for an imaged object in accordance with an embodiment of the invention.

Various embodiments of the invention provide a method that provides multiple rendering views of an object 160 or region of interest (e.g., a heart). The rendering views may be defined based on anatomically known structures or anatomically known view positions. For example, FIG. 3 illustrates a view plane 162 that is directed towards a volumetric dataset or object 160 and having a view direction 164. Within the data set, a crop plane 166 is defined, which can, for example, be randomly defined in space. The crop plane 166 divides the object 160 into two parts, a visible portion 168 that will be shown in a rendered image as defined by the view plane 162 and the cropped away portion 170 that will not be visible in the rendered image. In various embodiments of the invention, several such view planes 162 and crop planes 166 are used simultaneously.

Figure 4:
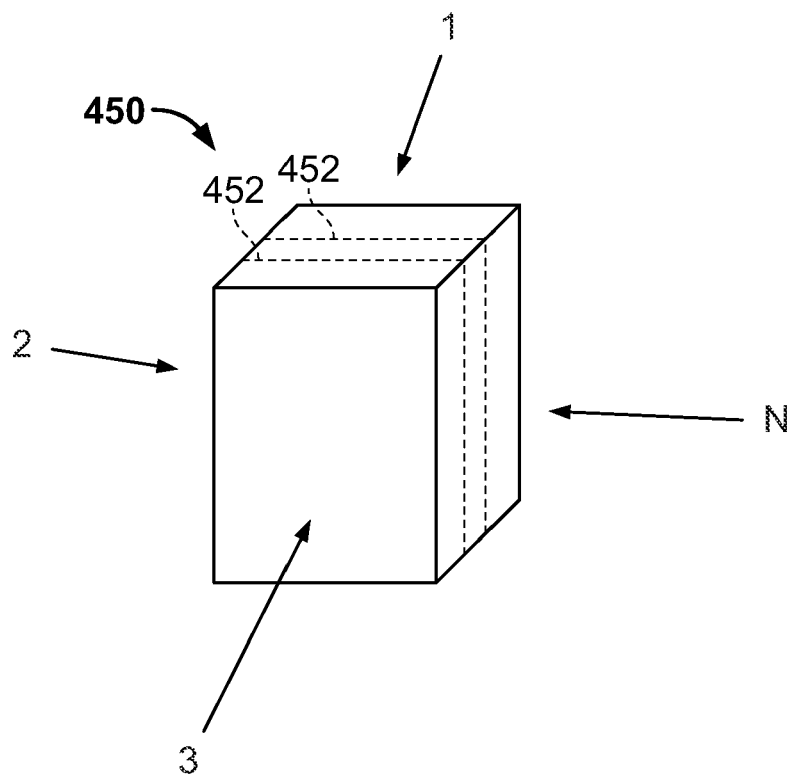
FIG. 4 is a diagram illustrating a plurality of views of an imaged object defined in accordance with an embodiment of the invention.

As another example, and as shown in FIG. 4, one or more view directions (illustrated by arrows 1, 2, 3 . . . N) may be defined anywhere in a data set and directed toward an object 450 of interest. For each view direction a volume rendering is automatically performed and multiple images generated, which may be displayed together (e.g., in a quad view) on a display. As shown in FIG. 4, a plurality of view directions may be selected. For example, a user may select with a mouse or trackball one or more views by selecting regions of the object 450 as illustrated by the arrows. The user then may modify the view direction by changing the angle of the direction relative to the surface of the object. The view direction may be changed, for example, using the mouse or trackball. For example, one or more view directions can be selected by choosing a predefined set of directions, such as, 180 degrees apart, such that opposite views are provided. Other angles also may be defined. Alternatively, the user can change the view directions interactively using the mouse or trackball. The view directions also may be linked together such that when one view directions is changed the other associated view direction (e.g., the other view direction in a predefined set) is also changed, for example, to maintain a 180 degree difference. Alternatively, the view directions may be changed independently.

Figure 5:
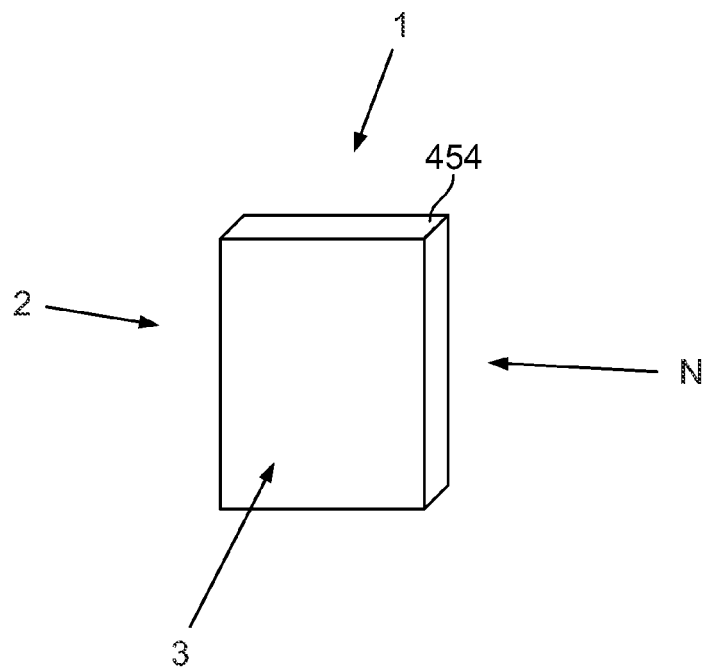
FIG. 5 is a diagram illustrating a plurality of views of a cropped imaged object defined in accordance with an embodiment of the invention.

The image of the object 450 also may be cropped by providing one or more crop planes 452 (e.g., two-dimensional (2D) cut planes). The object 450 also may be cropped with other portions of the image removed and view directions defined as shown in FIG. 5.

Figure 6:
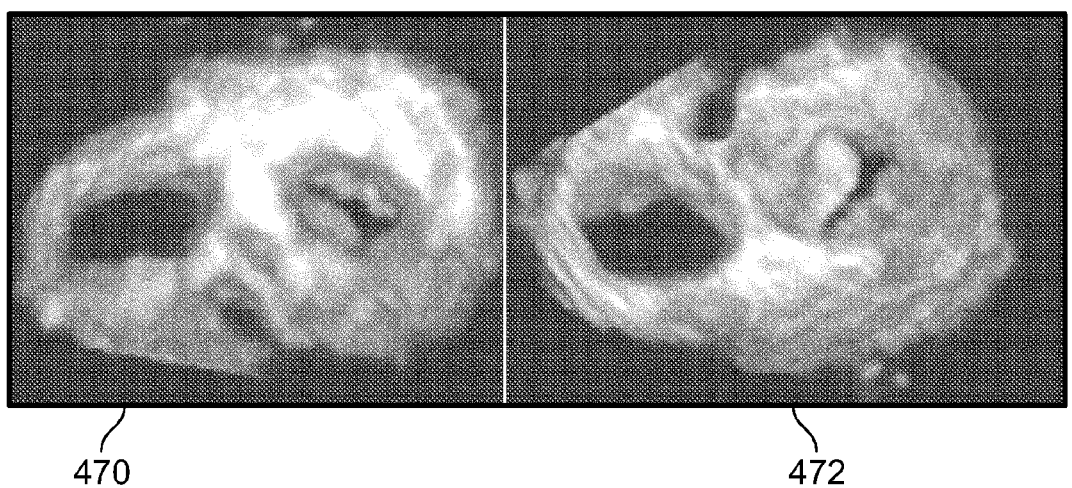
FIG. 6 is a display of images of a two views of a mitral valve generated in accordance with an embodiment of the invention and that corresponds to the cropping of FIG. 5.

The view directions can be changed simultaneously while maintaining the relative positions between the views, for example, maintaining the angle between the view planes. As an example, two views may be generated 180 degrees apart as shown in FIG. 6, which illustrates the mitral valve of the heart shown from both the atrial and ventricle side simultaneously in views 470 and 472, respectively. In this example, when the views are 180 degrees apart, two images of a structure from opposite sides are shown. When a user changes the view direction, both views are changed.

Figure 7:
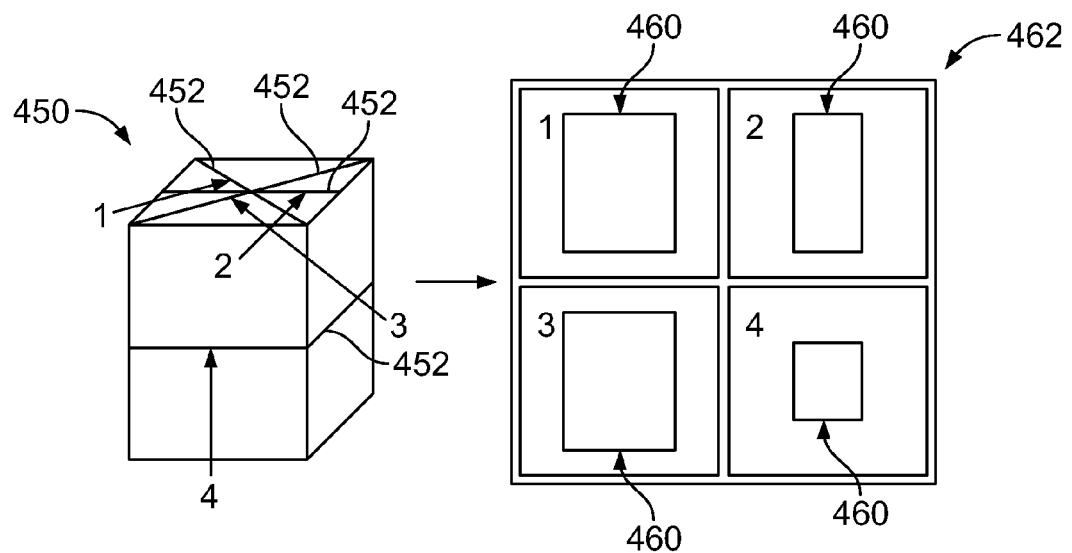
FIG. 7 is a diagram illustrating a plurality of views of an imaged object and a plurality of intersecting crop planes defined in accordance with an embodiment of the invention.
Figure 8:
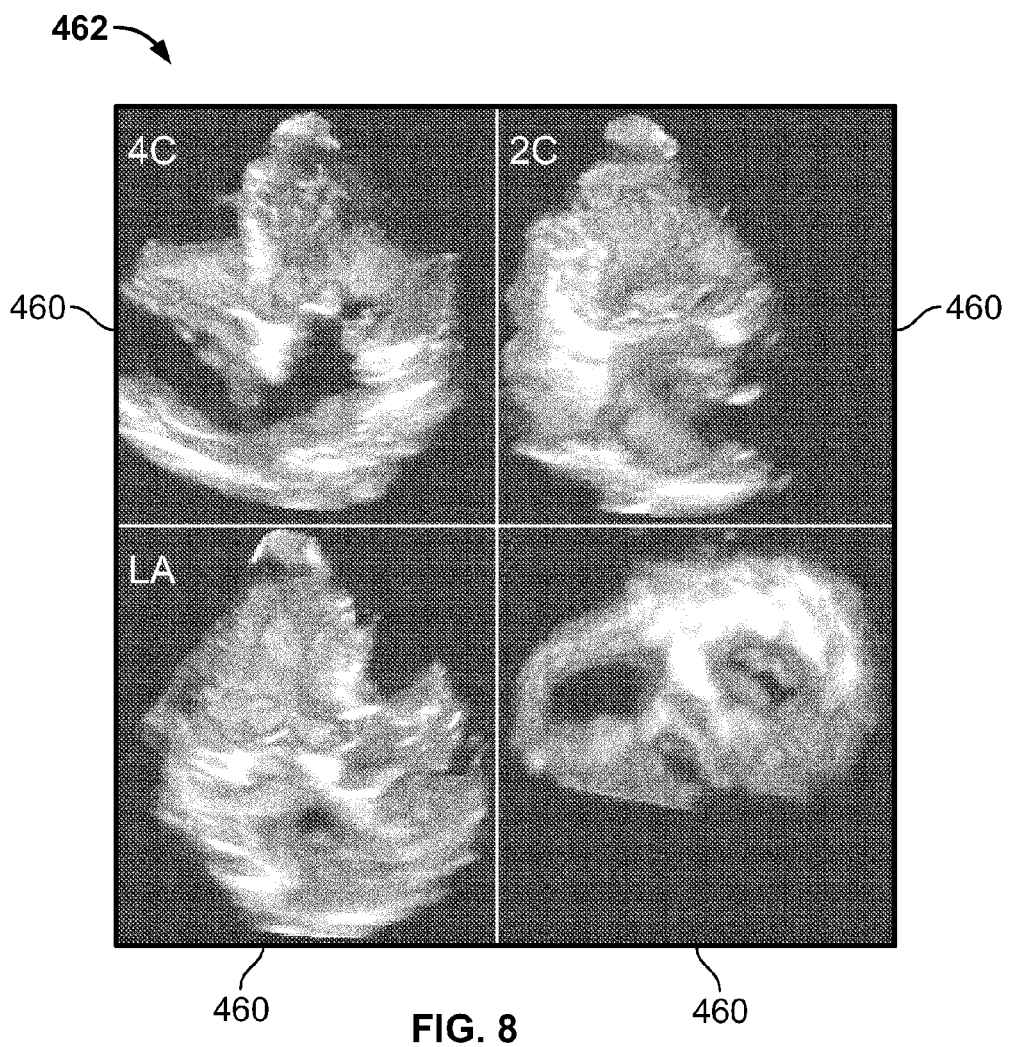
FIG. 8 is a display of images of standard views of a heart generated in accordance with an embodiment of the invention and that corresponds to the cropping of FIG. 7.

It should be noted that a plurality of crop planes 452 may be defined with corresponding view directions as shown in FIG. 7. The crop planes 452 are illustrated again by lines and a corresponding view direction illustrated by arrows. The view directions are shown perpendicular to the crop planes 452, but can be angled relative to the crop planes 452. A plurality of images 460 may then be generated and together displayed on a display 462 based on the user selected crop planes and view directions or generated based on, for example, a predetermined set of views. Essentially, a plurality of corresponding volume renderings are generated from a single 3D ultrasound data set stored in memory and simultaneously displayed. For example, as shown in FIG. 8, the plurality of images 460 may be images defined by the standard apical planes of the heart and a short axis view of the mitral valve. However, different layouts are contemplated and the various embodiments are not limited to views or arrangements in a quad configuration. Also, a user may define different views by selecting specific or particular view directions and crop planes 452 as described above. The position of the planes in the standard view may be defined using a method of alignment where the user readjusts the orientation of the 3D dataset in order to generate 2D cut planes that are in accordance with standard 2D views of, for example, the heart. These cut planes may then be used as crop planes.

Figure 9:
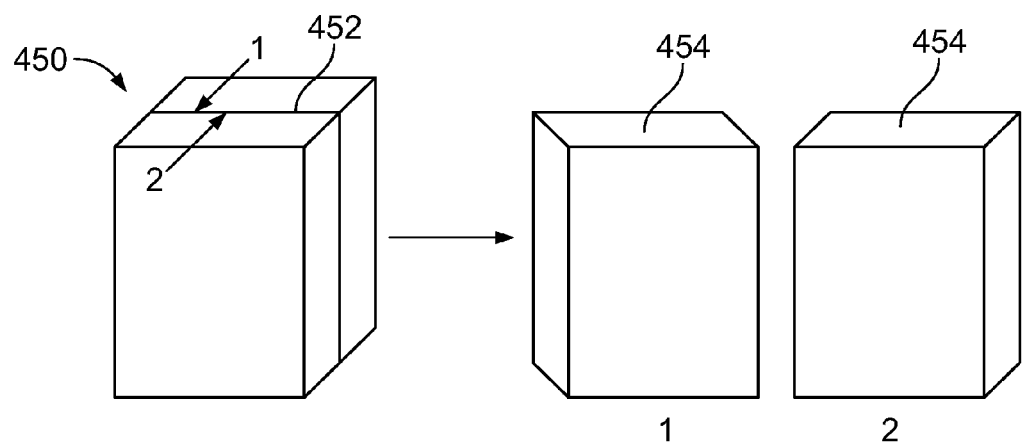
FIG. 9 is a diagram illustrating a plurality of views of an imaged object and a plurality of overlapping crop planes defined in accordance with an embodiment of the invention.
Figure 10:
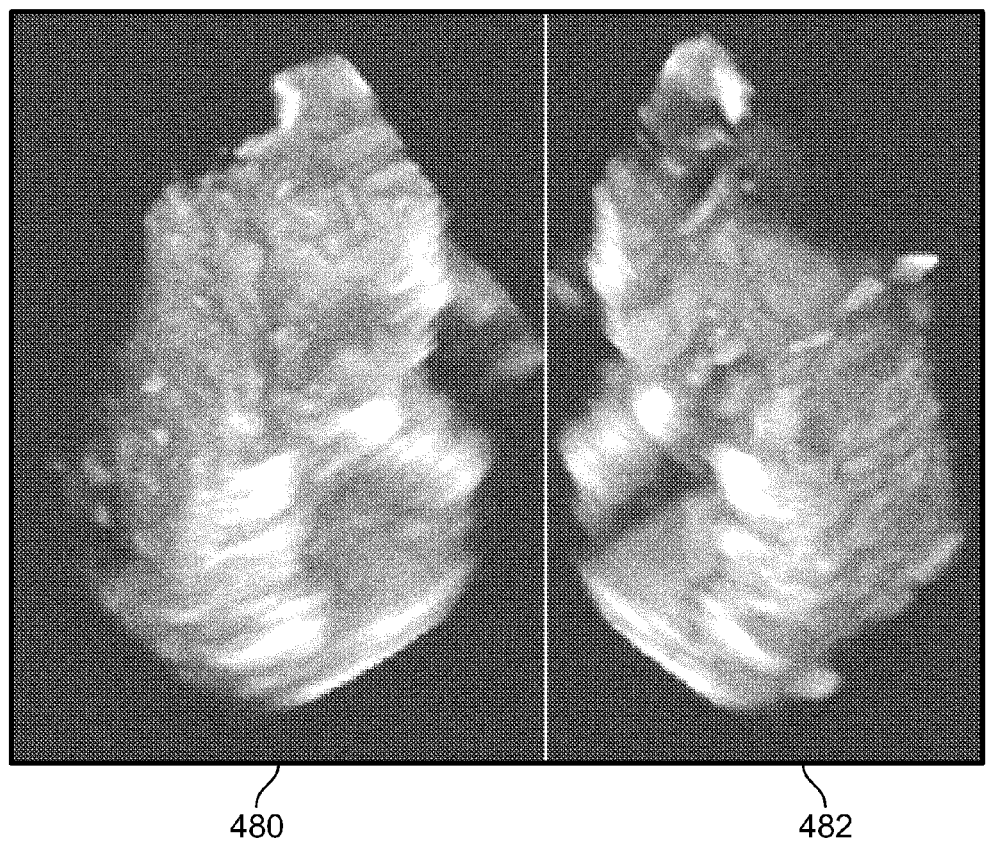
FIG. 10 is a display of dual images of a left ventricle of a heart generated in accordance with an embodiment of the invention and that corresponds to the cropping of FIG. 9.

Referring again to FIG. 7, the crop planes 452 (and hence the views) can be intersecting. Each display view will then show different parts of the object 450 independently of the other crop planes 452. However, the crop planes 452 may be overlapping as shown in FIG. 9 with the corresponding volume renderings defined by the view directions (1 and 2) displayed simultaneously. This configuration may be used to display two views of the object 450 simultaneously that encompass the entire object 450. For example, as shown in FIG. 10, a dual view of the left ventricle is displayed using one crop plane with views 480 and 482 shown from two different directions allowing a display of the entire heart chamber. Thus, the left ventricle apical 4-chamber view is displayed from two directions simultaneously where the standard apical 4-chamber view 480 shows the anterior wall and the view 482 shows the posterior/inferior wall.

It should be noted that the various display configurations and modes described herein may be generated during data acquisition using the ultrasound system 100, on previously acquired data using the ultrasound system 100 or on another system, for example, a reviewing station. It further should be noted that the particular crop planes and hence the simultaneous display may be based on predefined positions, for example, based on anatomically defined positions. For example, in echocardiography, three standard apical images or positions (i.e., 4-chamber view, 2-chamber view and long axis view) are identified using anatomical structures and the 3D ultrasound data cropped accordingly and volume renderings of these views simultaneously displayed on a screen.

Figure 11:
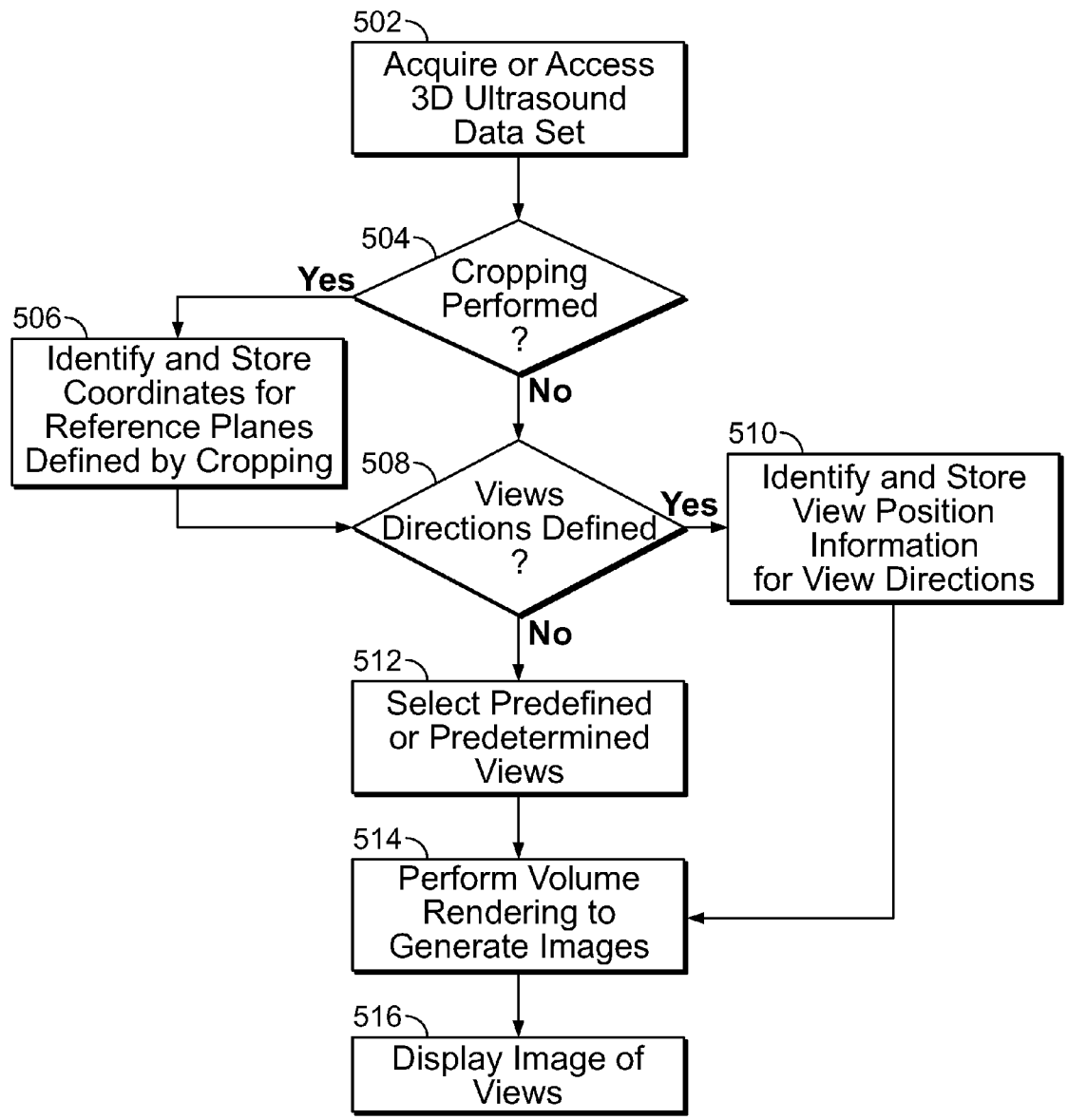
FIG. 11 is a flowchart of a method for automatically generating images of different views of an object in accordance with various embodiments of the invention.

A method 500 for automatically generating images of different views of an object is illustrated in FIG. 11. Specifically, at 502 scan data is acquired or accessed, for example, a stored 3D ultrasound data set may be accessed from memory or may be acquired. It should be noted that as the data is being acquired, the data may be temporarily stored for access. Thereafter at 504 a determination is made as to whether any cropping has been performed. For example, a determination may be made as to whether any crop planes have been provided or defined by a user. If cropping has been performed, then at 506 coordinates for the crop planes are identified and stored, which may include both translational and rotational coordinates. For example, the Cartesian coordinates for voxels within the image that are encompassed by the crop planes are stored. Alternatively, the planes can be stored using a surface normal and the distance to the origin.

It should be noted that anatomical markers may be used to identify the crop planes and a user may be prompted to approve the anatomical structures being used. For example, in a heart image, the mitral ring position can be identified using known detection methods or by a user and crop planes can be defined relative to the mitral ring position. Also, standard 2D echocardiology views such as the apical 4-chamber view can be identified by the user and used to define crop planes.

Once the coordinates are stored at 506 or if a determination is made at 504 that no cropping has been performed then at 508 a determination is made as to whether one or more view directions have been defined. If view directions have been defined, for example, by a user, then at 510 the view directions are identified. For example, the view position (e.g., coordinates) corresponding to the view directions for any identified planes are determined. If no view directions have been defined as determined at 508 then predefined or predetermined views are selected at 512. For example, standard views may be selected and identified as described herein.

Thereafter or after storing the view position information at 510, volume rendering is performed at 514. Specifically, separate image views are generated based on the view directions and optionally based on any crop planes selected. The volume renderings are performed on the same 3D ultrasound data set. For example, the volume renderings are performed by processing a single data set stored in memory. One method for producing volume renderings is to cast rays through the volume, for example, an object, and record the "ray values" when the rays pass a plane behind the object. The "ray value" recorded in the view plane is a combination of the values of all the voxels along the path from the viewpoint to the view plane. The combination may be, for example, the sum of the voxel values, each multiplied by a weighting value referred to as "opacity." Accordingly, for each of the view directions the same technique is applied on the same data set.

Thus, multiples views of an object or region of interest are generated from the same data set and each of the views may be linked or associated with the other views based on stored coordinate information. The different image views are generated in a single operation on a data set stored in memory. The views are generated by multiple volume renderings of the same dataset from different directions. The image views are then displayed at 516, for example, simultaneously displayed on a screen (e.g., a single display), such as in split screen or quad screen format.

Thus, the view directions and crop planes result in different image views being generated and displayed. The various viewing directions may be linked, for example, by using the same crop plane(s), but viewed from different angles where the relative positions are maintained. Further, the volume renderings are generated from the same data set (e.g., a single data set stored in memory) and not performed, for example, on the same data file loaded several times into memory.

A technical effect of at least one embodiment of the invention includes facilitating rendering of multiple views of an object by using a single data set. Using view directions, and optionally using cropping, a plurality of image views are generated and linked based on stored coordinate information. The image views then may be displayed simultaneously.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A method for generating multiple image views of an object, the method comprising:
    identifying a plurality of view directions relative to an image of an object;
    automatically volume rendering a volumetric data set with a processor based on the plurality of view directions;
    generating an image for each view direction with the processor using the rendered data;
    modifying one of the plurality of view directions;
    automatically modifying the other of the plurality of view directions with the processor to maintain the relative positions between the plurality of view directions; and
    generating with the processor a second image for each of the plurality of view directions using the rendered data after said automatically modifying the other of the plurality of view directions.

2. A method in accordance with claim 1 wherein the view directions are automatically selected.

3. A method in accordance with claim 1 further comprising receiving a user input defining the plurality of view directions.

4. A method in accordance with claim 1 further comprising identifying a plurality of crop planes with corresponding view directions.

5. A method in accordance with claim 4 further comprising receiving a user input based on a cropping command that defines the plurality of crop planes.

6. A method in accordance with claim 4 wherein at least some of the crop planes are overlapping and with different sides of the overlapping crop planes used for generating an image.

7. A method in accordance with claim 4 wherein the crop planes are intersecting and the resulting displays show a plurality of non-intersecting images displaying only a subset of crop operations.

8. A method in accordance with claim 4 further comprising using anatomical structure markers to identify the plurality of crop planes.

9. A method in accordance with claim 4 further comprising using anatomical structure markers to align the plurality of crop planes.

10. A method in accordance with claim 1 wherein the image volumetric data set comprises a single three-dimensional ultrasound data set stored in a memory.

11. A method in accordance with claim 1 further comprising simultaneously displaying the plurality of images.

12. A method in accordance with claim 1 further comprising automatically defining a plurality of crop planes used in the rendering.

13. A method for visualization of multiple volume renderings of a volumetric data set, the method comprising:
    identifying at least one crop plane on the volumetric data set;
    automatically generating a plurality of different views with a processor using the volumetric data based on the at least one crop plane;
    displaying on a single display images of the plurality of different views;
    modifying one of the plurality of different views; and
    automatically modifying with the processor the other of the plurality of different views maintain the relative positions between the plurality of views.

14. A method in accordance with claim 13 further comprising identifying view directions defining the different views, the view directions being one of user defined and predefined.

15. A method in accordance with claim 13 further comprising identifying view directions defining the different views and combining the view directions with the at least one crop plane.

16. A method in accordance with claim 13 further comprising volume rendering image data that is one of (i) stored and (ii) currently being acquired for use in automatically generating the different views.

17. A method in accordance with claim 16 wherein the volume rendering is performed on a single three-dimensional (3D) ultrasound data set stored in a memory.

18. A method in accordance with claim 13 further comprising automatically changing the different views based on a change in at least one of the views.

19. The method in accordance with claim 13 further comprising displaying on the single display a second image for each of the plurality of different views based on the volumetric data set after said automatically modifying the plurality of different views.

* * * * *